(12) United States Patent
Yamada et al.

(10) Patent No.: US 9,440,939 B2
(45) Date of Patent: Sep. 13, 2016

(54) NORBORNENE DERIVATIVE

(71) Applicants: JNC CORPORATION, Tokyo (JP); JNC PETROCHEMICAL CORPORATION, Tokyo (JP)

(72) Inventors: Hirotsuna Yamada, Chiba (JP); Sakae Kawamura, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/647,825

(22) PCT Filed: Nov. 28, 2013

(86) PCT No.: PCT/JP2013/082009
§ 371 (c)(1),
(2) Date: May 28, 2015

(87) PCT Pub. No.: WO2014/084297
PCT Pub. Date: Jun. 5, 2014

(65) Prior Publication Data
US 2015/0307467 A1    Oct. 29, 2015

(30) Foreign Application Priority Data
Nov. 28, 2012    (JP) ................... 2012-259723

(51) Int. Cl.
*C07D 301/03*     (2006.01)
*C07D 303/16*     (2006.01)
(Continued)

(52) U.S. Cl.
CPC ........... *C07D 303/16* (2013.01); *C07D 301/14* (2013.01); *C07D 303/14* (2013.01); *C07D 303/17* (2013.01)

(58) Field of Classification Search
CPC .................. C07D 303/16; C07D 301/14
USPC .................................................. 549/523
See application file for complete search history.

(56) References Cited

U.S. PATENT DOCUMENTS 3,187,018 A    6/1965    Tinsley et al.
3,255,162 A    6/1966    Beavers et al.

FOREIGN PATENT DOCUMENTS

JP    05-247135    9/1993
JP    07-101903    4/1995
(Continued)

OTHER PUBLICATIONS

"International Search Report (Form PCT/ISA/210)", mailed on Feb. 18, 2014, with English translation thereof, pp. 1-4.
(Continued)

*Primary Examiner* — T. Victor Oh
(74) *Attorney, Agent, or Firm* — Jianq Chyun IP Office

(57) ABSTRACT

A novel compound useful as a raw material for a resist material is described. A norbornene derivative having epoxy and a methylene-mediated reactive group in a norbornane skeleton is represented by the following formula.

(1)

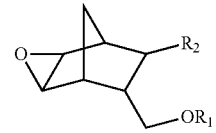

In the formula, $R_1$ represents a hydrogen atom, acryloyl, methacryloyl or hydroxymethylacryloyl, and $R_2$ represents a hydrogen atom or an alkyl group having 1 to 4 carbon atoms.

3 Claims, 1 Drawing Sheet

(51) Int. Cl.
    *C07D 303/17*  (2006.01)
    *C07D 303/14*  (2006.01)
    *C07D 301/14*  (2006.01)

(56)  References Cited

FOREIGN PATENT DOCUMENTS

| JP | 2002-322103 | 11/2002 |
|---|---|---|
| JP | 2003-192680 | 7/2003 |
| JP | 2008-234909 | 10/2008 |
| JP | 2010-13392 | 1/2010 |
| JP | 2011-16738 | 1/2011 |
| KR | 10-2009-0072418 | 7/2009 |

OTHER PUBLICATIONS

Kas'Yan, L.I. et al.,"Reaction of stereoisomeric bicyclic a-oxides with lithium aluminum hydride", Zhurnal Organicheskoi Khimii, 1982, p. 1213-p. 1218, vol. 18 Issue.6, MAIK Nauka/Interperiodica Publishing.

Christian Elsner, Claudia Ernst and Michael R. Buchmeiser, "Miniaturized Biocatalysis on Polyacrylate-Based Capillary Monoliths", Journal of Applied Polymer Science, Feb. 5, 2011, p. 1450-p. 1458, vol. 119 Issue3, Wiley Periodicals, Inc.

Yu, Chuan-Ying et al., "Synthesis of 5,6-Epdxybicyclo[2.2.1] Heptanse-2-Methyl 5,6-Epdxybicyclo [2.2.1] Heptane-2-Carboxylate and Its 3-Methyl Derivative", Acta Chimica Sinica, Jun. 1964, p. 348-351, vol. 30 Issue.3, Chinese Chemical Society.

F.J.C. van Gasstel, A.J.H. Klunder and B. Zwanenburg, "Enzymatic optical resolution of norbornanecarboxylic esters using Pig Liver Esterase", Recueil des Travaux Chimiques des Pays-Bas, May 1991, p. 175-184, vol. 110 Issue.5, WILEY-VCH Verlag GmbH & Co. KGaA.

"International Preliminary Report on Patentability of PCT counterpart application"; this report contains the following items :Form PCT/IB/338, PCT/IB/373, PCT/ISA237(cover sheet), PCT/ISA237(Box No. I),PCT/ISA237(Box No. V), mailed on Jun. 2, 2015, which is English translation of "Written Opinion of the International Searching Authority", p. 1-p. 6.

"Office Action of Chinese Counterpart Application", issued on Dec. 2, 2015, with machine translation thereof, pp. 1-17.

Blanco et al., "Divergent synthesis of two precursors of 3'-homo-2'-deoxy- and 2'-homo-3'-deoxy-carbocyclic nucleosides", Tetrahedron, Oct. 2002, pp. 8843-8849, vol. 58, Issue 43.

Fehr et al., "Enantioselective Synthesis of (−)-beta-Santalol by a Copper-Catalyzed Enynol Cyclization-Fragmentation Reaction", Angewandte Chemie, Sep. 2009, pp. 7221-7223, vol. 48.

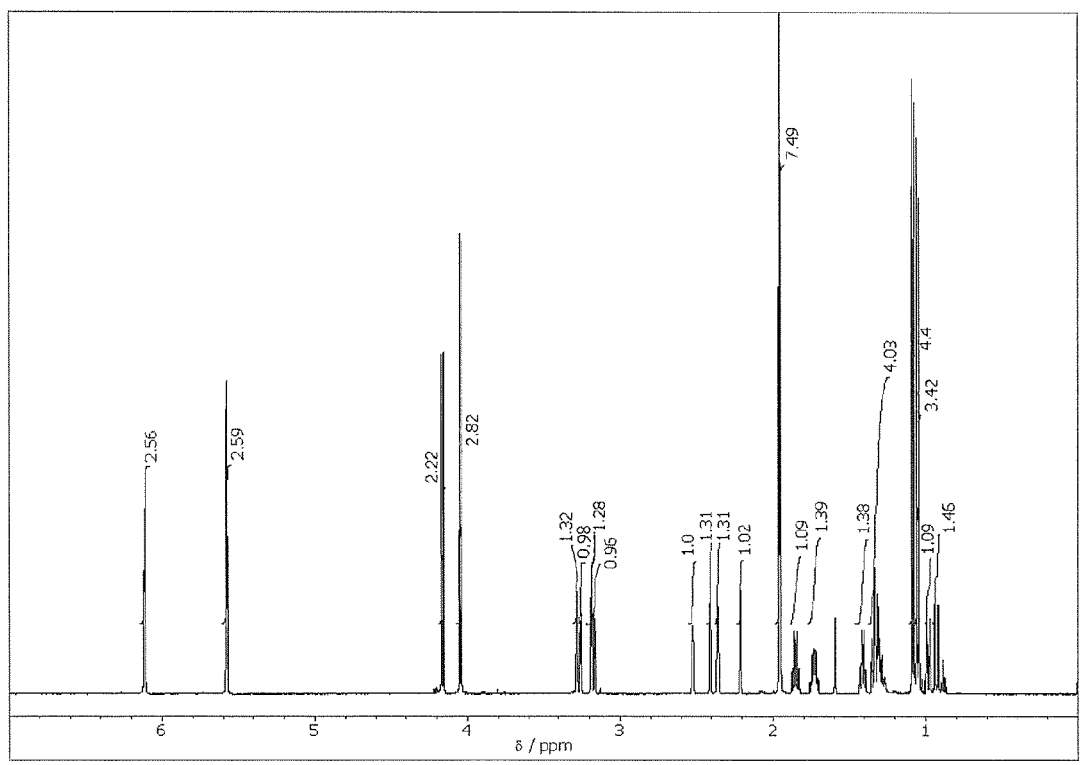

NORBORNENE DERIVATIVE

CROSS-REFERENCE TO RELATED APPLICATION

This application is a 371 application of the international PCT application serial no. PCT/JP2013/082009, filed on Nov. 28, 2013, which claims the priority benefits of Japan Patent Application no. 2012-259723, filed on Nov. 28, 2012. The entirety of each of the above-mentioned patent applications is hereby incorporated by reference herein and made a part of this specification.

BACKGROUND OF THE INVENTION

1. Field of the Invention

The invention relates to a novel norbornene derivative.

2. Description of the Related Art

Generally, methacrylate is widely used as a raw material monomer of a functional resin. The methacrylate may be applied in a wide range of fields such as paints, adhesives, electronic materials and medical treatments, etc., and is particularly used in various applications as a special functional material, such as an optical material, a resist material, a coating material or a laminating material, etc., by being copolymerized with other polymerizable monomers.

A resist material is used in fields where micromachining is made by photolithographic patterning, such as manufactures of printed circuit boards, LCD and semiconductor devices, etc. Particularly, in a lithography step for semiconductor manufacturing, finer machining is required, so studies have been carried out on short wavelength exposure where the exposure wavelength is shortened to improve the resolution, and studies have been intensively carried out on chemically amplified resist materials useful in short wavelength exposure (e.g., Patent Document 1).

PRIOR-ART DOCUMENT

Patent Document

Patent Document 1: JP 2011-16738 A

SUMMARY OF THE INVENTION

Problems to be Solved

Particularly, among electronic materials, the resist material is a material having both optical characteristics and mechanical characteristics such as adhesion to a substrate and being required to have special functionality.

An issue of invention is to provide a novel compound useful as a raw material for a resist material.

Means for Solving the Problems

As a result of earnest studies to solve the above problem, the inventors of the invention have discovered a norbornene derivative having epoxy and a methylene-mediated reactive group in a norbornane skeleton.

The invention includes the following items.

Item [1] is a norbornene derivative represented by formula (I).

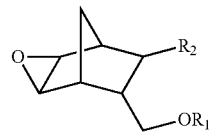

In the formula, $R_1$ represents a hydrogen atom, acryloyl, methacryloyl or hydroxymethylacryloyl, and $R_2$ represents a hydrogen atom or an alkyl group having 1 to 4 carbon atoms.

Item [2] is the norbornene derivative of item [1] in which in formula (I), $R_1$ is a hydrogen atom, acryloyl or methacryloyl, and $R_2$ is methyl or ethyl.

Item [3] is the norbornene derivative of item [1] in which in formula (I), $R_1$ is a hydrogen atom, acryloyl or methacryloyl, and $R_2$ is methyl.

Item [4] is a method for producing a norbornene derivative, which includes:

a) a Diels-Alder reaction step of reacting cyclopentadiene with a compound of formula (A) to obtain a norbornene derivative (B);

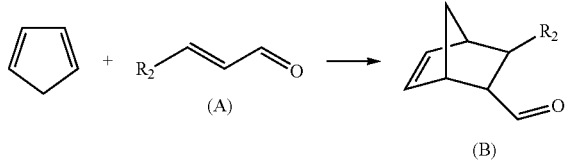

b) a reduction step of reducing the norbornene derivative (B) to obtain a norbornene-methylol derivative (C) represented by formula (C);

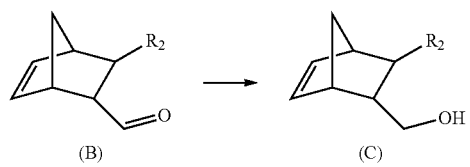

c) an esterification step of esterifying the hydroxyl group of the norbornene-methylol derivative (C); and d) an epoxidation step of oxidizing the unsaturated bond of the norbornene skeleton of the norbornene-methylol derivative (C), wherein the method for producing a norbornene derivative is characterized in that step a) and step b) are followed by either step c) or step d), and the norbornene derivative is represented by formula (E).

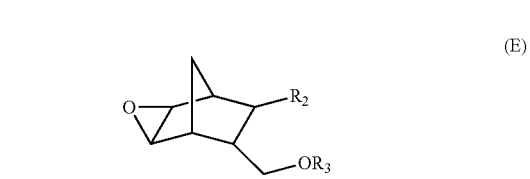

In formulae (A), (B), (C) and (E), $R_2$ represents a hydrogen atom or an alkyl group having 1 to 4 carbon atoms, and $R_3$ represents acryloyl, methacryloyl or hydroxymethylacryloyl.

Item [5] is the method of item [4] in which the epoxidation step d) is performed after the esterification step c).

Item [6] is a method for producing a norbornene derivative, which includes:

a) a Diels-Alder reaction step of reacting cyclopentadiene with a compound of formula (A) to obtain a norbornene derivative (B);

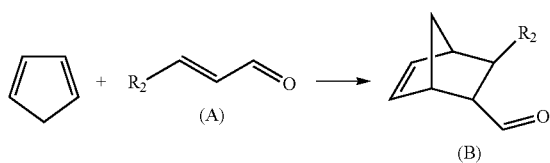

b) a reduction step of reducing the norbornene derivative (B) to obtain a norbornene-methylol derivative (C) represented by formula (C); and

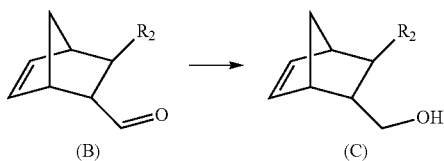

d) an epoxidation step of oxidizing the unsaturated bond of the norbornene skeleton of the norbornene-methylol derivative (C),
wherein the norbornene derivative is represented by formula (F), and

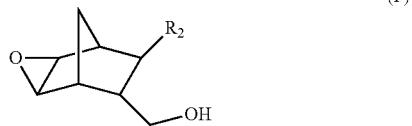

in formulae (A), (B), (C) and (F), $R_2$ represents a hydrogen atom or an alkyl group having 1 to 4 carbon atoms.

Effects of the Invention

With the invention, a bifunctional monomer having epoxy and a methylene-mediated reactive group in a norbornane skeleton can be provided.

BRIEF DESCRIPTION OF THE DRAWINGS

FIG. 1 is an NMR chart of the epoxymethylnorbornanemethyl methacrylate (EMNMA) obtained in Example 1.

DESCRIPTION OF THE EMBODIMENTS

The norbornene derivative of the invention is represented by formula (I).

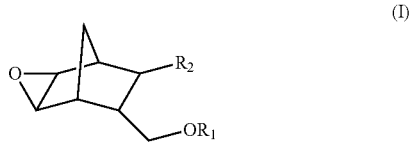

In the above formula (I), $R_1$ represents a hydrogen atom, acryloyl, methacryloyl or hydroxymethylacryloyl. $R_1$ is preferably a hydrogen atom, acryloyl or methacryloyl. $R_2$ represents a hydrogen atom or an alkyl group having 1 to 4 carbon atoms. $R_2$ is preferably methyl or ethyl, and more preferably methyl.

<Method for Producing Norbornene Derivative of the Invention>

The norbornene derivative of the invention can be produced by going through a Diels-Alder reaction step, a reduction step, an esterification step and an epoxidation step.

<1. Diels-Alder Reaction Step>

The Diels-Alder reaction step is, as described below, a step using cyclopentadiene (CPD) or dicyclopentadiene (DCPD), where cyclopentadiene is reacted with a compound of the following formula (A) having a double bond to obtain the norbornene derivative (B). In formulae (A) and (B), $R_2$ has the same definition as above.

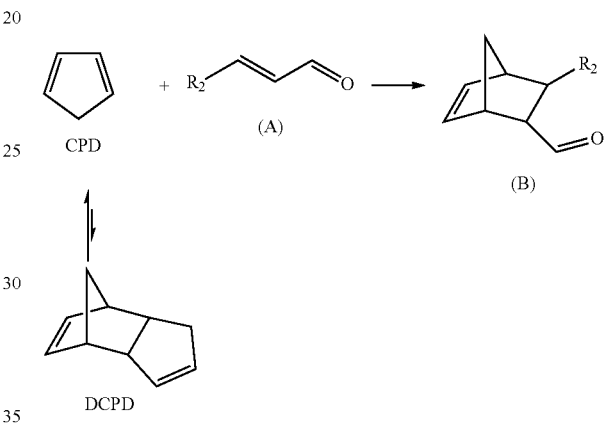

The mixing ratio (compound (A)/DCPD) of the compound (A) relative to DCPD as the raw material is normally 1 to 10 and preferably 2 to 5 in terms of the molar ratio (mol/mol). The compound (A) may be selected in accordance with the desired norbornene derivative, and specifically, may be preferably exemplified by crotonaldehyde, 2-penten-1-al, 2-hexen-1-al, and 2-hepten-1-al, etc. Commercially available products may be used as these compounds. In the Diels-Alder reaction step, an endo-isomer or exo-isomer of the derivative (B) may be produced, and both may be suitably used.

In the Diels-Alder reaction step of the invention, general reaction conditions for the Diels-Alder reaction may be adopted. The reaction temperature is normally 150 to 200° C., and preferably 160 to 180° C. A pressure may be applied during the reaction. The reaction may be performed under pressure of normally 0.01 to 1 MPa, preferably 0.05 to 0.8 MPa. The reaction time is normally 1 to 8 hours, and preferably 4 to 6 hours. The reaction may also be performed under an inert gas atmosphere such as a nitrogen atmosphere, etc. In addition, during the reaction, a solvent inert to the reaction intermediates and products may also be used. Examples of the solvent include: saturated hydrocarbons, such as hexane, heptane and octane, etc.; aromatic hydrocarbons, such as benzene, toluene and xylene, etc.; and esters, such as ethyl acetate and butyl acetate, etc.

<2. Reduction Step>

The reduction step is a step of reducing the aldehyde part of the norbornene derivative (B) to obtain the following norbornene-methylol derivative (C). In formulae (B) and (C), $R_2$ has the same definition as above.

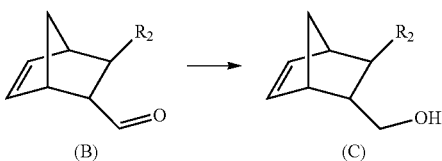

(B) → (C)

Examples of the reducing agent used for the reduction step include: lithium hydride, sodium hydride, potassium hydride, lithium borohydride, sodium borohydride ($NaBH_4$), potassium borohydride, lithium aluminum hydride ($LiAlH_4$), sodium aluminum hydride, potassium aluminum hydride, and diisobutylaluminum hydride, etc. Among them, from the viewpoint of selectively reducing aldehyde, sodium borohydride and lithium aluminum hydride, etc. are preferred. The mixing ratio (reducing agent/derivative (B)) of the reducing agent relative to the derivative (B) is normally 0.2 to 1, and preferably 0.4 to 0.6, in terms of molar ratio (mol/mol).

The temperature of the reduction step is normally 40 to 100° C., and preferably 40 to 60° C. The reaction time is normally 2 to 6 hours, and preferably 2 to 4 hours. The reaction may be performed under stirring, etc.

<3. Esterification Step>

The esterification step is a step of esterifying the hydroxyl group of the norbornene-methylol derivative (C). The hydroxyl group of the norbornene-methylol derivative (C) is reacted with a compound having an acryloyl group, a methacryloyl group or a hydroxymethylacryloyl group (these substituents are hereinafter referred to as $R_3$), so as to synthesize an ester (D) of the derivative (C) and the compound having $R_3$. The esterification step is optional. If a compound of formula (I) in which $R_1$ is a hydrogen atom, namely a compound of the above formula (F), is to be obtained, the esterification step may be omitted. In addition, even if the esterification step is performed after an epoxidized derivative (C) is obtained by the later-described epoxidation step, the compound of formula (I) of the invention can still be obtained.

Examples of the compound having $R_3$ and reacted with the derivative (C) include: acid halides, such as methacrylic chloride, acrylic chloride, methacrylic bromide, acrylic bromide, acrylic iodide, methacrylic iodide, hydroxymethylacrylic chloride, and hydroxymethylacrylic bromide, etc.; acrylic anhydride; and methacrylic anhydride, etc. Among them, from the viewpoint of reactivity and ease of purification, methacrylic chloride and acrylic chloride, etc. are preferred.

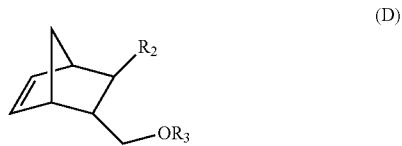

(D)

In formula (D), $R_3$ represents a substituent of the above $R_1$ other than the hydrogen atom. That is, $R_3$ represents acryloyl, methacryloyl or hydroxymethylacryloyl. $R_3$ is preferably acryloyl or methacryloyl.

The mixing ratio (compound having $R_3$/derivative (C) or epoxidized derivative (C)) of the compound having $R_3$ relative to the derivative (C) or the epoxidized derivative (C) is normally 1 to 5 and preferably 1 to 2, in terms of molar ratio (mol/mol).

The esterification step may be implemented under well-known esterification reaction conditions. The temperature of the esterification step is normally -30 to 100° C., preferably -5 to 5° C. The reaction time is normally 0.5 to 24 hours, and preferably 1 to 5 hours.

If necessary, a catalyst may also be used in the esterification step. The catalyst may be suitably selected according to the reaction. If an acid halide is used as the compound having $R_3$, triethylamine, trimethylamine, pyridine, piperidine, piperazine, ethylenediamine, tetramethylethylenediamine, hexamethylenediamine, 4-(dimethylamino)pyridine, or lipase, etc. may be used. These may be used alone or as a mixture of two or more thereof The addition amount of the catalyst is normally 0.1 to 5 and preferably 1 to 2, in terms of the molar ratio (catalyst/derivative (C)) relative to the derivative (C). If the derivative (C) has been epoxidized previously, the addition amount of the catalyst is the same.

If necessary, a polymerization inhibitor may also be added in the esterification step. The polymerization inhibitor is not particularly limited, as long as being capable of inhibiting polymerization. Examples thereof include phenothiazine, hydroquinone, butylated hydroxytoluene, p-methoxyphenol, 2,2'-methylenebis(6-t-butyl-p-cresol), 2,2,6,6-tetramethylpiperidine-1-oxyl, 6-ethoxy-2,2,4-trimethyl-1,2-dihydroquinoline, and cupferron, etc.

The addition amount of the polymerization inhibitor is normally 0.001 to 10 and preferably 0.001 to 3, in terms of the weight ratio (polymerization inhibitor/derivative (C)) relative to the derivative (C). If the derivative (C) has been epoxidized previously, the addition amount of the polymerization inhibitor is the same.

The solvent used for the esterification step may be suitably selected according to the compounds used. Examples thereof include: aromatic hydrocarbons, such as benzene, toluene, xylene, trialkylbenzene, ethylbenzene and cumene, etc.; aliphatic saturated hydrocarbons, such as hexane, heptane, octane, nonane and decane, etc.; alicyclic hydrocarbons, such as cyclohexane, methylcyclohexane, dimethylcyclohexane and ethylcyclohexane, etc.; and ethers, such as tetrahydrofuran, diethyl ether, di-n-butyl ether, 1,4-dioxane, ethylene glycol dimethyl ether, ethylene glycol diethyl ether, and methyl t-butyl ether, etc. These solvents may be used alone or as a mixture.

<4. Epoxidation Step>

The epoxidation step is a step of oxidizing and epoxidizing the unsaturated bond of the norbornene skeleton of the derivative (C) or ester (D). The epoxidation step may alternatively be performed before the esterification step. In the following formula, $R_1$, $R_2$ and $R_3$ have the same definitions as above. If the compound shown at the left side of the following formula is the derivative (C), that is, if no esterification step has been performed, a compound of formula (I) in which $R_1$ is a hydrogen atom, namely a compound of the above formula (F), is obtained.

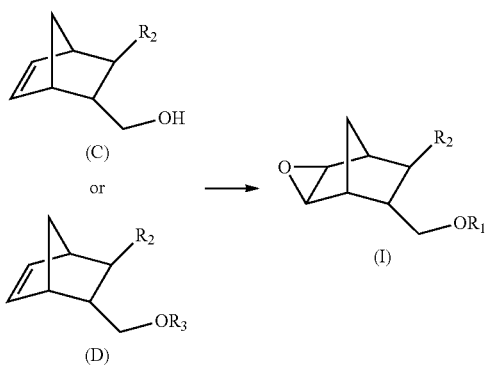

In the epoxidation step, an epoxidizing agent is made act on the derivative (C) or ester (D) to epoxidize the double bond moiety of the norbornene skeleton. The epoxidizing agent is not particularly limited, and examples thereof include: organic peroxy acids, such as peracetic acid, performic acid, trifluoroperacetic acid, perbenzoic acid, and m-chloroperbenzoic acid, etc.; organic peroxides, such as t-butylhydroperoxide, and cumene hydroperoxide, etc.; dioxirane compounds, such as dimethyldioxirane, methylethyldioxirane, methylisobutyldioxirane, etc.; inorganic peroxides, such as ammonium peroxide, alkali metal peroxide, ammonium persulfate, alkali metal persulfate, ammonium perborate, alkali metal perborate, ammonium percarbonate, alkali metal percarbonate, alkaline earth metal peroxide, and zinc peroxide, etc.; inorganic peroxy acids, such as persulfuric acid, percarbonic acid, and permonophosphoric acid, etc.; hydrogen peroxide; and molecular oxygen, etc. Preferred examples include m-chloroperbenzoic acid and hydrogen peroxide. These may be used alone or as a mixture of two or more thereof The mixing ratio (epoxidizing agent/derivative (C) or ester (D)) of the epoxidizing agent relative to the derivative (C) or ester (D) is normally 1 to 10 and preferably 1 to 1.5, in terms of molar ratio (mol/mol).

The epoxidation step may be implemented under well-known epoxidation reaction conditions. The temperature of the epoxidation step is normally -30 to 40° C., and preferably 0 to 20° C. The reaction time is normally 1 to 10 hours, and preferably 1 to 5 hours.

The epoxidation step is preferably performed in the presence of a solvent. Examples of the solvent include: halogenated hydrocarbon solvents, such as dichloromethane, chloroform, dichloroethane, 1,1,2,2-tetrachloroethane and 1-chlorobutane, etc.; aliphatic hydrocarbon solvents, such as pentane, hexane, cyclohexane and methylcyclohexane, etc.; aromatic hydrocarbon solvents, such as benzene, toluene, xylene, chlorobenzene and dichlorobenzene, etc.; acid amide solvents, such as N,N-dimethylfonnamide, N,N-dimethylacetamide and N-methylpyrrolidone, etc.; nitrile solvents, such as acetonitrile and benzonitrile, etc.; organic acid solvents, such as formic acid, acetic acid and propionic acid, etc.; nitro compound solvents, such as nitromethane and nitrobenzene, etc.; and carbon disulfide, etc. Among them, dichloromethane and dichlorobenzene, etc. are preferred. These may be used alone or as a mixture of two or more thereof.

The product obtained in each step of the invention may be extracted with a treatment usually used to extract a product from a reaction solution obtained after each step. In addition, the production may also be carried out by a well-known purification method such as reduced-pressure distillation, chromatography or recrystallization, etc.

As described above, in the production of the compound according to the invention, in the case of performing the esterification step, the esterification step may be performed before or after the epoxidation step. That is, whether the esterification step of esterifying the norbornene-methylol derivative represented by the above formula (C) or the epoxidation step of epoxidizing the unsaturated bond of the norbornene skeleton of the norbornene-methylol derivative represented by formula (C) is performed earlier, the following norbornene derivative (E) can be obtained. From the viewpoint of ease of reaction, it is preferred to perform the epoxidation step after the esterification step.

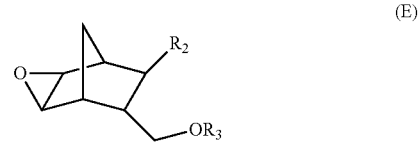

In formula (E), $R_2$ represents a hydrogen atom or an alkyl group having 1 to 4 carbon atoms, and $R_3$ represents acryloyl, methacryloyl or hydroxymethylacryloyl. $R_2$ is preferably methyl or ethyl, and more preferably methyl. In addition, $R_3$ is preferably acryloyl or methacryloyl.

The norbornene derivative of the invention is a bifunctional monomer having epoxy and a methylene-mediated reactive group in a norbornane skeleton. Due to the norbornane skeleton, the norbornene derivative is expected to have excellent optical characteristics. In addition, due to inclusion of hydroxyl group or unsaturated ester via methylene, flexibility is increased and cross-linking is easy. Therefore, it is expected that a rigid polymer having high adhesion to a substrate may be obtained.

Regarding the compound of formula (I) of the invention, in the case of an alicyclic epoxy-methylol compound in which $R_1$ is a hydrogen atom, namely a compound of the above formula (F), since a polymerizable substituent may be added to the hydroxyl by esterification or the like, the compound is useful as a monomer raw material of a special functional material.

Particularly, regarding the compound of formula (I) of the invention, in the case where $R_1$ is acryloyl, methacryloyl or hydroxymethylacryloyl, etc. (a compound of the above formula (E)), a polymer can be obtained by polymerization of the substituent, and can be further cross-linked by the epoxy in the norbornene skeleton so that a rigid 3D structure is formed. Therefore, it is expected that a material advantageous to micromachining may be provided as the resist material.

The monomer raw material according to the invention is expected to be used in various applications as a special functional material such as an optical material, a resist material, a coating material and a laminating material, etc. In the various applications, the compound of the present invention may be used by a well-known method. For example, in the case of the resist material, a polymer obtained by subjecting the compound of the invention to polymerization or copolymerization by a well-known method is dispersed or dissolved in a suitable solvent to prepare a sensitizing solution, and the sensitizing solution is coated onto a substrate using, e.g., a coating apparatus such as a roller, a roll coater or a spin coater, etc., followed by drying. Thereby, a resist film can be obtained.

According to use, the compound represented by formula (E) may also be copolymerized with other polymerizable monomers. For example, components of a resist material that is used for direct patterning are provided as a combination of a polymer component obtained by copolymerizing other polymerizable monomers, a polymerizable monomer component, a polyfunctional polymerizable monomer component, a thermo- or photo-initiator, and a solvent, etc., wherein a compound represented by formula (E) can be used as a part of the polymerizable monomer component or the polyfunctional polymerizable monomer component. In addition, for a photoresist material, the components are provided as a combination of a polymer component obtained by copolymerizing a plurality of polymerizable monomers, a photo-acid generator and a solvent, etc., wherein the compound represented by formula (E) may be used as one of the plurality of polymerizable monomers.

Examples of the compound that may be combined or copolymerized with the compound represented by formula (E) include: (meth)acrylic acid, a (meth)acrylic acid ester monomer, a vinyl ether derivative, a styrene derivative and maleic anhydride, etc. The (meth)acrylic acid ester monomer is a compound obtained by substituting the hydrogen in the carboxyl group of (meth)acrylic acid with methyl, ethyl, n-propyl, i-propyl, n-butyl, i-butyl, t-butyl, cyclopentyl, cyclohexyl, tricyclodecyl[$5.2.1.0^{2,6}$], adamantyl, norbornyl, isonorbornyl, hydroxyethyl, propoxyethyl, butoxyethyl, 2-methyl-2-adamantyl, 2-ethyl-2-adamantyl, 3-hydroxy-1-adamantyl, tetrahydropyranyl or tetrahydrofuranyl. The vinyl ether derivatives include ethyl vinyl ether, cyclohexyl vinyl ether, and hydroxyethyl vinyl ether, etc. The styrene derivatives include styrene, p-hydroxystyrene, p-methoxystyrene and p-t-butoxystyrene, etc. These copolymerizable compounds may be used alone or as a combination of two or more thereof.

The method for polymerizing or copolymerizing the compound represented by formula (E) to obtain a polymer component is not particularly limited, and a conventional method may be implemented. For example, the polymer component can be obtained by mixing the respective compounds in the solvent so as to make a desired molar ratio, adding a polymerization initiator, subjecting the resultant to polymerization or copolymerization by heating or light irradiation, and separating the product, and, if necessary, then performing a purification treatment.

EXAMPLES

The invention will be specifically described with examples, but is not limited thereto. Moreover, identification of a compound was performed using a proton nuclear magnetic resonance spectrum (hereinafter referred to as "NMR"), and the purity of a compound was measured by gas chromatography (hereinafter referred to as "GC") or high performance liquid chromatography (hereinafter referred to as "HPLC"). The NMR was measured using a Varian NMR System (500 MHz), with tetramethylsilane as a standard substance and chloroform-d as a solvent. The measurement was performed under conditions of a measurement temperature of 27° C., a measurement frequency of 500 MHz and a cumulative number of 8 times.

Example 1

(Diels-Alder Reaction Step)
862.2 g (6.52 mol) of dicyclopentadiene (DCPD) and 1920 g (27.39 mol) of crotonaldehyde (CA) (4.2 equivalents relative to DCPD) were placed in a 5 L reactor for a pressurization reaction apparatus (made by Taiatsu Techno). Stirring was performed at a speed of 400 rpm, and the air in the vessel was replaced with $N_2$ under a pressure change of 0.3 to 0.7 MPa for 10 cycles. After the replacement, purging was carried out until the pressure reached 0 MPa, and the temperature was raised to 170° C., and then the resultant was stirred at 165° C. for 4 hours. After that, the resultant was cooled to 30° C., the residual pressure in the vessel was purged, and a crude solution was extracted (conversion: 92.4%; selectivity: 93.7%; reaction yield: 86.5%).

Next, purification was performed by reduced-pressure distillation. Finally, 510.7 g (3.75 mol) of methylnorbornene aldehyde (MNA) was obtained from 862.2 g (6.52 mol) of the raw material. The isolated yield was 57.5%, based on DCPD.

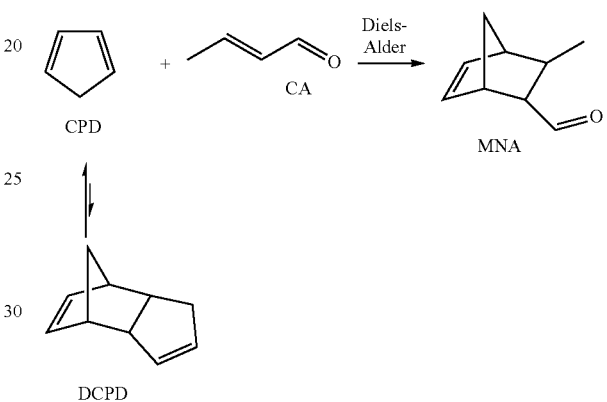

(Reduction Step)
510.7 g of MNA (3.75 mol) was placed in a 2 L three-necked round-bottom flask. 720 ml of a 10 wt % aqueous solution containing 70.93 g (1.88 mol) of sodium borohydride $NaBH_4$ (SBH) (0.5 equivalent relative to MNA) was slowly added to the resultant by dripping while its temperature was maintained at 50° C. or lower.

After the resultant was stirred at 50° C. for 3 hours, 375 ml of saturated ammonium chloride ($NH_4Cl$) aqueous solution was added.

The aqueous solution was extracted three times with 265 ml of ethyl acetate. The collected organic layers were combined and washed with 375 ml of a saturated saline solution. 50 g of magnesium sulfate ($MgSO_4$) was added to the organic layer for dehydration and then removed by filtration, and then the resultant was concentrated by distilling away the ethyl acetate as the extracting solvent.

The conversion was 99.8%, the selectivity was 99.8% and the reaction yield was 99.6%.

Purification was performed by reduced-pressure distillation. Finally, 404.3 g (2.93 mol) of methylnorbornene methanol (MNAH) was obtained from 510.7 g (3.75 mol) of the raw material. The isolated yield was 78%.

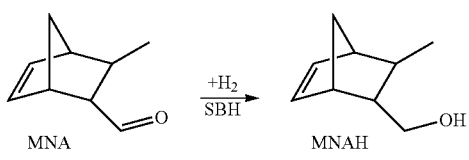

(Esterification Step)

404.3 g of MNAH (2.93 mol), 592.0 g (5.85 mol) of triethylamine (TEA) (2 equivalents relative to MNAH), 4.08 g (20.5 mmol) of phenothiazine (about 1 wt % relative to MNAH) as a polymerization inhibitor, and 5270 ml of toluene as a solvent were placed in a 10 L four-necked round-bottom flask. 366.9 g (3.51 mol) of methacrylic acid chloride (MAC) (1.2 equivalents relative to MNAH) was slowly added to the resultant by dripping at 0° C. or lower. The reaction temperature was maintained at 5° C. or lower.

After the reaction was performed at 0° C. for 1 hour, the crude reaction solution was washed with 880 ml of a saturated sodium bicarbonate aqueous solution and 880 ml of a saturated saline solution. 50 g of magnesium sulfate was added to the organic layer for dehydration and then removed by filtration, and then the resultant was concentrated by distilling away toluene under a reduced pressure.

The conversion was 99.9%, the selectivity was 95.7% and the reaction yield was 95.6%. Purification was performed by reduced-pressure distillation. Finally, 404.3 g (1.96 mol) of methylnorbornenemethyl methacrylate (MNMA) was obtained from 404.3 g (2.93 mol) of the raw material. The isolated yield was 67%.

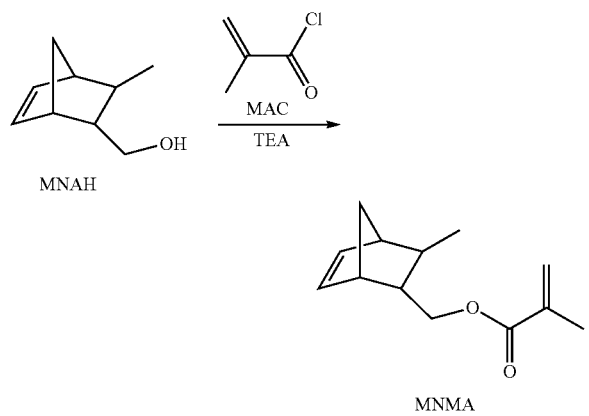

(Epoxidation Step)

404.3 g of MNMA (1.96 mol), 311.6 g (2.94 mol) of sodium carbonate ($Na_2CO_3$) (1.5 equivalents relative to MNMA), and 4100 ml of dichloromethane as a solvent were placed in a 10 L four-necked round-bottom flask. The resultant was sufficiently cooled in an ice bath. 372.0 g (2.16 mol) of m-chloroperbenzoic acid (mCPBA) (1.1 equivalents relative to MNMA) was added. The crude reaction solution was stirred at 0° C. for 1 hour, and was further stirred at room temperature for 3 hours. 1600 ml of a 10% sodium thiosulfate ($Na_2S_2O_3$) aqueous solution was added to the crude reaction solution, and the resultant was washed with 1600 ml of saturated saline solution. 50 g of magnesium sulfate was added to for dehydration and then removed by filtration, and then the resultant was concentrated by distilling away the solvent and so on under a reduced pressure.

The conversion was 99.5%, the selectivity was 97.0% and the reaction yield was 96.5%.

Purification was performed by silica gel column chromatography (eluting solvent: n-heptane). Finally, 338.5 g (1.52 mol) of (7-methyl-3-oxatricyclo[3.2.1.0$^{2,4}$]octane-6-yl) methyl methacrylate (EMNMA; epoxymethylnorbornanemethyl methacrylate) was obtained from 404.3 g (1.96 mol) of the raw material. The isolated yield was 77.7%.

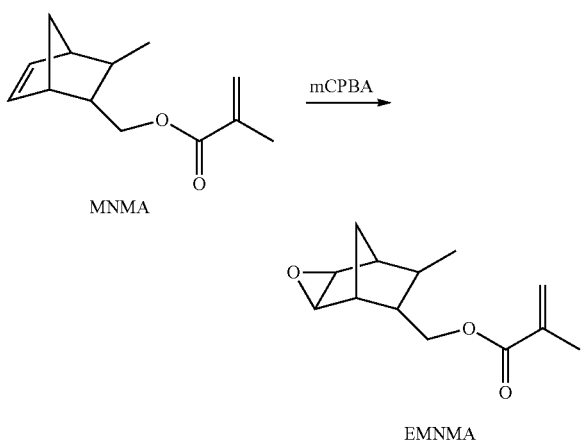

The NMR chart of the obtained compound is shown in FIG. 1. From this analysis result, it was confirmed that the obtained compound has a structure of the above EMNMA. In addition, the ratio between an endo-isomer and an exo-isomer of the compound was 56:44.

$^1$H NMR (CDCl$_3$): End: 0.93 (br, 1H); 1.08 (d, 3H); 1.25-1.35 (m, 1H); 1.41 (m, 1H); 1.72 (m, 1H); 1.96 (m, 3H); 2.36 (m, 1H); 2.41 (m, 1H); 3.19 (m, 1H); 3.29 (m, 1H); 4.05 (d, 2H); 5.58 (td, 1H); 6.11 (m, 1H).

Exo: 0.98 (br, 1H); 1.05 (d, 3H); 1.25-1.35 (m, 1H); 1.25-1.35 (m, 1H); 1.85 (m, 1H); 1.96 (m, 3H); 2.21 (m, 1H); 2.53 (m, 1H); 3.17 (m, 1H); 3.26 (m, 1H); 4.16 (d, 2H); 5.58 (td, 1H); 6.11 (m, 1H).

The purity of the obtained compound was measured with a gas chromatography (GC) analysis under the following conditions, and was confirmed to be 97.5% in terms of GC purity.

The column was HR-1 (25 m; inner diameter: 0.32 mm; film thickness: 0.25 μm). The temperature of the sample introducing part was 250° C. The temperature of the detection part was 300° C. The column temperature condition was from 50° C. to 300° C. in a rate of 5° C./min. The retention time of EMNMA was 15.5 minutes.

The obtained compounds were as follows.

TABLE 1

| Compound Name | Molecular Formula | Molecular Weight |
| --- | --- | --- |
| MNA | $C_9H_{12}O$ | 136.19 |
| MNAH | $C_9H_{14}O$ | 138.21 |
| MNMA | $C_{13}H_{18}O_2$ | 206.28 |
| EMNMA | $C_{13}H_{18}O_3$ | 222.28 |

INDUSTRIAL APPLICABILITY

The compound according to the invention may be used in various applications as a special functional material such as an optical material, a resist material, a coating material or a laminating material, etc.

The invention claimed is:

1. A method for producing a compound, comprising:
   a) a Diels-Alder reaction step of reacting cyclopentadiene with a compound of formula (A) to obtain a compound (B);

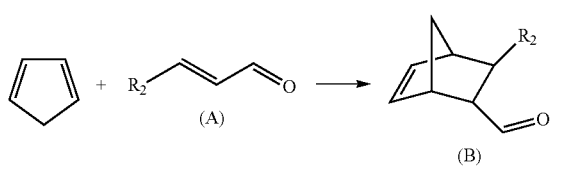

b) a reduction step of reducing the compound (B) to obtain a compound (C) represented by formula (C);

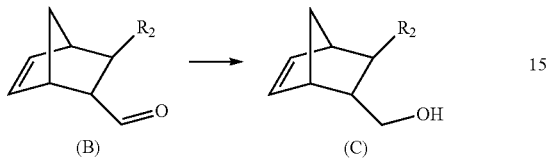

c) an esterification step of esterifying the hydroxyl group of the compound (C); and
d) an epoxidation step of oxidizing the unsaturated bond of the norbornene skeleton of the compound (C),
wherein step a) and step b) are followed by either step c) or step (d), and the compound being produced is represented by formula (E),

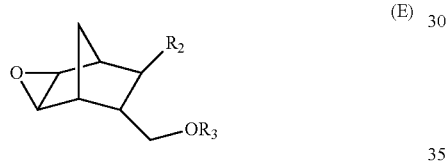

wherein in formulae (A), (B), (C) and (E), $R_2$ represents a hydrogen atom or an alkyl group having 1 to 4 carbon atoms, and $R_3$ represents acryloyl, methacryloyl or hydroxymethylacryloyl.

2. The method of claim 1, wherein the epoxidation step d) is performed after the esterification step c).

3. A method for producing a compound, comprising:
a) a Diels-Alder reaction step of reacting cyclopentadiene with a compound of formula (A) to obtain a compound (B);

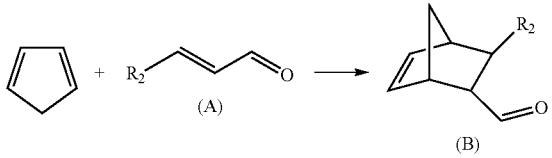

b) a reduction step of reducing the compound (B) to obtain a compound (C) represented by formula (C); and

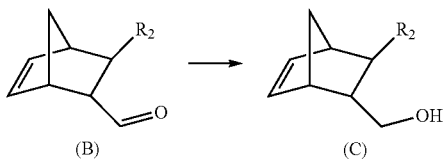

d) an epoxidation step of oxidizing the unsaturated bond of the norbornene skeleton of the compound (C),
wherein the compound being produced is represented by formula (F), and

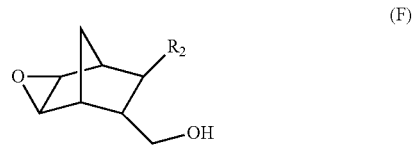

in formulae (A), (B), (C) and (F), $R_2$ represents a hydrogen atom or an alkyl group having 1 to 4 carbon atoms.

* * * * *